United States Patent [19]

Green et al.

[11] Patent Number: 5,658,312

[45] Date of Patent: *Aug. 19, 1997

[54] SKIN FASTENER

[75] Inventors: David T. Green, Westport; Henry Bolanos, East Norwalk; Wayne Person, Newtown, all of Conn.

[73] Assignee: United States Surgical Corporation, Norwalk, Conn.

[*] Notice: The portion of the term of this patent subsequent to Oct. 22, 2010, has been disclaimed.

[21] Appl. No.: 426,434

[22] Filed: Apr. 20, 1995

Related U.S. Application Data

[63] Continuation of Ser. No. 97,303, Jul. 23, 1993, abandoned, which is a continuation of Ser. No. 817,578, Jan. 7, 1992, abandoned, which is a continuation of Ser. No. 601,335, Oct. 22, 1990, Pat. No. 5,108,422.

[51] Int. Cl.[6] ............................................. A61B 17/08
[52] U.S. Cl. ...................................... 606/219; 606/213
[58] Field of Search ........................ 606/72, 75, 213, 606/219, 220, 142, 143, 151; 411/455, 457; 227/921

[56] References Cited

U.S. PATENT DOCUMENTS

| D. 286,442 | 10/1986 | Korthoff et al. ............... 606/219 |
|---|---|---|
| 2,302,559 | 7/1942 | La Place . |
| 3,209,754 | 10/1965 | Brown . |
| 3,273,562 | 9/1966 | Brown . |
| 3,528,693 | 9/1970 | Pearson et al. . |
| 3,744,495 | 7/1973 | Johnson . |
| 3,757,629 | 9/1973 | Schneider . |
| 4,060,089 | 11/1977 | Noiles . |
| 4,217,902 | 8/1980 | March . |
| 4,243,775 | 1/1981 | Rosensaft et al. ............ 525/415 |
| 4,263,903 | 4/1981 | Griggs . |
| 4,273,920 | 6/1981 | Nevin ........................ 528/361 |
| 4,275,813 | 6/1981 | Noiles . |
| 4,428,376 | 1/1984 | Mericle . |
| 4,485,816 | 12/1984 | Krumme . |
| 4,570,623 | 2/1986 | Howmedica . |
| 4,627,437 | 12/1986 | Bedi et al. . |
| 4,635,637 | 1/1987 | Schreiber . |
| 4,671,280 | 6/1987 | Dorband et al. . |
| 4,712,550 | 12/1987 | Sinnett . |
| 4,719,917 | 1/1988 | Barrows et al. . |
| 4,932,960 | 6/1990 | Green et al. . |
| 4,994,073 | 2/1991 | Green . |

FOREIGN PATENT DOCUMENTS

| 2519545 | 7/1983 | France . |
|---|---|---|
| 1311721 | 5/1987 | U.S.S.R. ........................ 606/75 |

*Primary Examiner*—Gary Jackson
*Assistant Examiner*—Kevin Truong

[57] ABSTRACT

A fastener for securing adjacent layers of body tissue to each other and being configured and composed of a material so as to emerge from the body tissue after a limited period of time. The fastener includes a backspan and at least two prongs extending from the backspan. Each prong has a tapered tip culminating in a sharp point. The prongs each include a shaft having a cylindrical portion of uniform diameter. In one embodiment, the prong includes a serrated portion having a plurality of notches spaced apart so as to define ridge portions therebetween.

8 Claims, 9 Drawing Sheets

SKIN FASTENER

This is a continuation of application Ser. No. 08/097,303, filed on Jul. 23, 1993, now abandoned, which is a continuation of Ser. No. 07/817,578, filed on Jan. 7, 1992, now abandoned, which is a continuation of Ser. No. 07/601,335, filed on Oct. 22, 1990, now U.S. Pat. No. 5,108,422.

BACKGROUND OF THE INVENTION

1. Field of the Invention

This invention relates to surgical fasteners used to join body tissue and more particularly to surgical fasteners which are composed of a material and configured to work their way out of body tissue after a limited period of time.

2. Background of the Art

Surgical fasteners have been used in operating procedures to eliminate the need for suturing, which is both time consuming and inconvenient. In many applications the surgeon can use a stapler apparatus, i.e., a fastener implanting device loaded with one or more surgical fasteners, to accomplish in a few seconds what would have taken many minutes to perform by suturing. This reduction in operating time reduces blood loss and trauma to the patient.

Surgical fasteners have been in the form of metal staples which are bent by the delivery apparatus to hook together body tissue. Such staples are typically made from biocompatible metals such as stainless steel alloys or titanium.

Two-part fasteners are also known, as illustrated in U.S. Pat. No. 4,506,670, in which a barbed fastener is used in conjunction with a retaining piece to hold the fastener in place.

Typically, the two-part fastener comprises a backspan and two barbed prongs which are engaged and locked into a separate retainer piece. In use, the fastener is pressed into the body tissue so that the barbs penetrate the tissue and emerge from the other side where they are then locked into the retainer piece. The retainers prevent the fastener from working loose from the tissue. The two piece fasteners cannot be unlocked and are not easily removable. For this reason, they must be made of a bioabsorbable material.

Possible materials include polymers and copolymers of glycolic acid (i.e. hydroxyacetic acid), the cyclic dimer of glycolic acid ("glycolide"), lactic acid, the cyclic dimer of lactic acid ("lactide") and related monomers. Polymers and copolymers of the foregoing kind and absorbable surgical devices made therefrom are well known. See, e.g., U.S. Pat. Nos. 2,668,162; 2,703,316; 2,758,987; 3,225,766; 3,297,033; 3,422,181; 3,531,561; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,060,089; 4,137,921; 4,157,437; 4,234,775; 4,237,920; 4,300,565; and 4,523,591; U.K. Patent No. 779,291; D. K. Gilding et al., "Biodegradable polymers for use in surgery—polyglycolic/poly(lactic acid) homo- and co-polymers: 1, *Polymer*, Volume 20, pages 1459–1464 (1979), and D. F. Williams (ed.) Biocompatibility of Clinical Implant Materials, Vol. II, ch. 9: "*Biodegradable Polymers*" (1981).

U.S. Pat. No. 4,667,674 to Korthoff et al discloses a two part surgical fastener comprising a fastener member and a retainer member. The fastener member has a base, and a pair of prongs extending perpendicularly from the base. The prongs are spaced inward from the respective ends of the base in order to prevent splaying of the prongs, and to improve hemostasis.

The two piece fasteners require the staple delivery apparatus to have access to both sides of the tissue. Usually, such devices have a U-shaped member into which tissue is inserted. The stapler apparatus has a fastener holder and an anvil which are pivotally connected at one end, and mounted on the legs of the U-shaped support structure. See, for example, U.S. Pat. No. 4,402,445 to Green which discloses a surgical fastener and means for applying same. In a surgical operation, the tissue to be joined is positioned between the fastener holder and the anvil, which contains the fastener retainers. The fasteners are ejected from the holder into the tissue, and the prongs are locked into the retainers.

In some applications, however, it is not possible to have access to body tissue from two opposite directions. For example, in skin grafting applications one can only apply fasteners from a stapler positioned above the skin.

The prior art includes many examples of surgical staplers which do not enclose the body tissue between an anvil and fastener holder. For example, surgical staplers such as those described in U.S. Pat. No. 3,643,851 and U.S. Pat. No. 4,618,086 approach the skin from one direction. However, they require the use of staples which are malleable enough to be crimped by an anvil so that the prongs hook into the tissue. Typically, such staples are made of metal and are not bioabsorbable. They must be removed by another device such as a stapler extractor which is not only time consuming but can cause discomfort and pain to the patient. The discomfort and pain in removal of the staples are especially acute when the fasteners are used in skin grafting a burn victim. The sensitivity of the burn patient's skin cannot be understated; any contact with their skin causes distress, let alone removal of fasteners inserted through the skin and embedded in underlying body tissue.

Single piece barbed fasteners made from bioabsorbable material are known. U.S. Pat. No. 4,635,637 discloses a fastener having a base member and two substantially parallel shafts upstanding from the base member, the ends of the shafts each having a barb. The barbed fastener is disclosed as being useful in the repair of meniscal tissue. Pending patent application Ser. Nos. 372,025 filed Jun. 27, 1989, now issued U.S. Pat. No. 5,089,009 and 314,368 filed Feb. 22, 1989, now issued U.S. Pat. No. 4,994,073 also disclose bioabsorbable fasteners having barbs. If these fasteners are removed, then the patient will suffer from the same distress as described above with respect to non-bioabsorbable staples.

The prior art fasteners discussed above were designed with the intention that significant vertical support was required. Thus, outwardly extending barbs were provided on their prongs to ensure that they remained embedded in the body tissue for a sufficiently long period of time. However, such barbed fasteners remained in the tissue for a longer time than was necessary. The need therefore exists for a fastener which remains embedded in the tissue only for a sufficient period of time to allow healing to commence but avoids the discomfort and pain associated with the removal of prior fasteners.

SUMMARY OF THE INVENTION

The present invention overcomes the drawbacks and deficiencies of the prior art. The present inventors discovered that in skin grafting, the emphasis is on lateral support across an incision or skin graft interface to provide sufficient lateral force between adjacent tissue sections. It was found that the vertical support provided by the barbed prongs was unnecessary and that this configuration often required actual removal of the fasteners, causing pain and discomfort. The present invention therefore overcomes the problems of prior art staples and fasteners by significantly limiting the extent of pain the patient will experience. The present invention achieves this objective by providing a surgical fastener which is composed of a material and configured so as to work its way out of body tissue after a specific period of time or can be more easily removed beforehand.

The surgical fastener includes a backspan and at least two prongs which extend from the backspan, preferably perpendicular to the backspan and parallel to each other. Each prong includes a tapered tip portion to facilitate penetration into the body tissue and is configured to remain in the body for a relatively short period of time. The material of the prong also has a low coefficient of friction to facilitate ejection from the body tissue. In one embodiment, substantially the entire shaft portion up to the tapered tip portion has a portion of uniform diameter. That is, there are no barbs on the shaft which would retain the embedded fastener for a longer period of time than necessary. In other embodiments, a serrated portion is formed in the uniform-diameter shaft portion to provide additional retention, but less retention than that of the barbs of the prior art.

The present invention also provides a method for skin grafting comprising inserting a plurality of fasteners each having spaced apart prongs wherein at least one prong is devoid of barbs, securing a dressing over the fasteners to provide sufficient vertical force to hold the fasteners for a period of time until healing commences, and removing the dressing after healing commences wherein a substantial number of the fasteners will be dislodged when the dressing is removed and a substantial number of the remaining fasteners will be automatically ejected by the body in a relatively short period of time.

BRIEF DESCRIPTION OF THE DRAWINGS

Preferred embodiments of the invention are described hereinbelow with reference to the drawings, wherein.

DETAILED DESCRIPTION OF THE PREFERRED EMBODIMENTS

Figure 3:
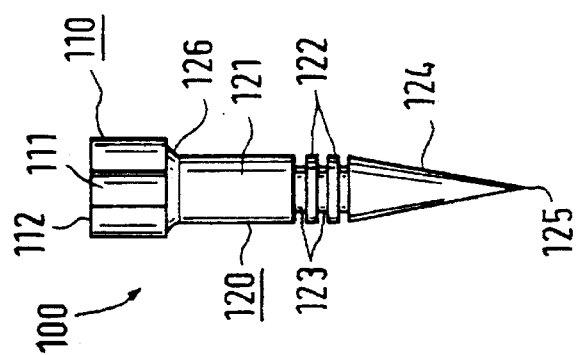
FIG. 3 is a side view of the fastener of FIG. 1.
Figure 1:
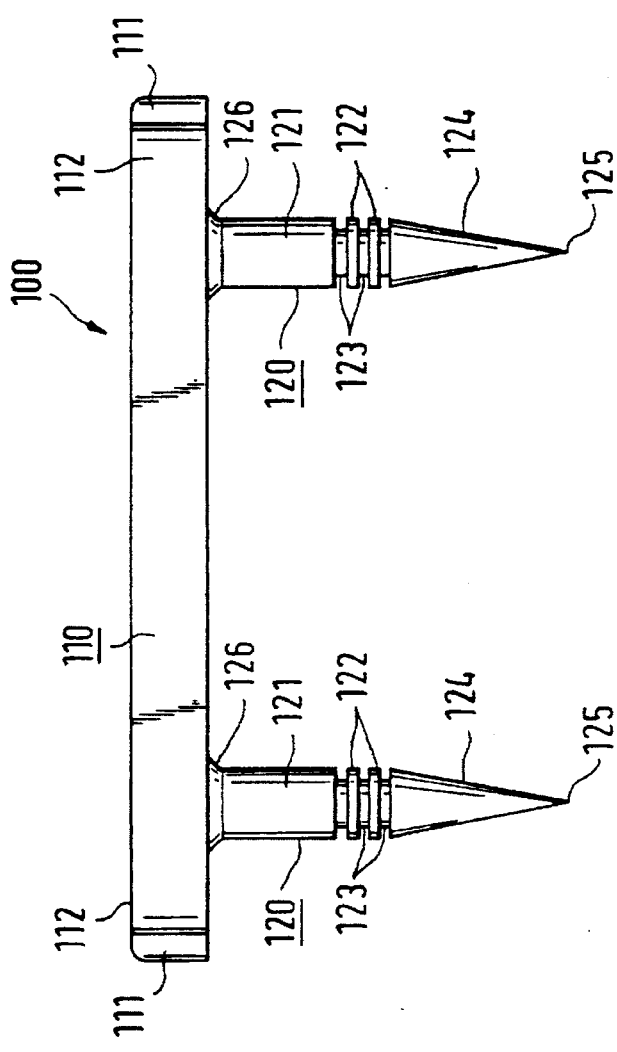
FIG. 1 is an elevational front view of one embodiment of a fastener of the present invention.
Figure 2:
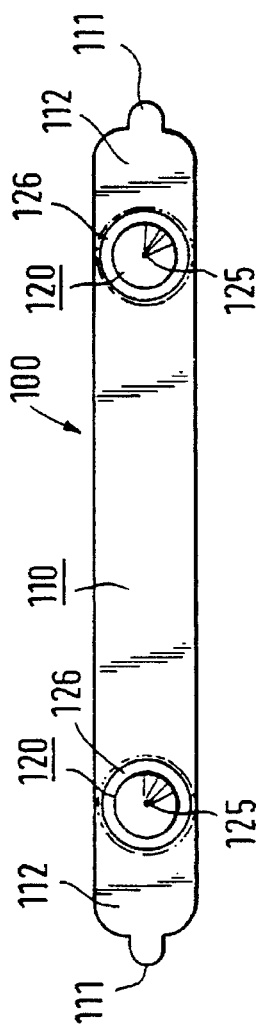
FIG. 2 is a top view of the fastener of FIG. 1.

Turning now to the drawings, FIGS. 1, 2 and 3 illustrate one embodiment of the skin fastener of the present invention. Fastener 100 includes a backspan 110 and two pronged portions 120 extending from backspan 110. Although the pronged portions 120 are shown parallel to each other and extending substantially perpendicular to backspan 110, as in all the embodiments disclosed herein, one or both of the pronged portions 120 can alternately be secured at a different angle to backspan 110 to extend inwardly towards each other or outwardly away from each other. In this embodiment, each prong 120 has a shaft portion 121 illustratively cylindrical in configuration, and a tapered tip portion 124 which culminates in a sharp point 125 at the distal end to facilitate penetration of body tissue. Prongs 120 also include a serrated portion having ridges 122 alternating with recessed notch portions 123. The serrations extend circumferentially around shaft 121. Fastener 100 is a double serrated prong fastener in that there are two ridge portions 122 on each prong. The serrations provide additional frictional means to hold the fastener in body tissue for a longer period of time than if no serrations were present. Nevertheless, these serration do not constitute barbs. That is, the ridges do not extend radially beyond the circumferential surface of the cylindrical shaft portion 121, and they do not prevent fastener 100 from gradually working its way out of body tissue within a specific period of time. By not having barbs, the fasteners can also be more easily removed. The diameter of the tapered tip portion 124 does not exceed the diameter of the shaft portion 121. The base portion of each prong 120 may be provided with a carved surface 126.

In the embodiment shown in FIG. 1, the backspan 110 extends lengthwise a greater distance than the distance between prongs 120. In other words, thug embodiment possesses an overlap portion 112 which extends the area of tissue which is being held down and is an optional feature of this invention since alternately the backspan 110 can terminate at the prongs 120. Members 111 at each end of the fastener backspan 110 can optionally be provided to provide a guide means to maintain the proper orientation of the fastener inside a fastener applying instrument while the fastener is being implanted.

Figure 4:
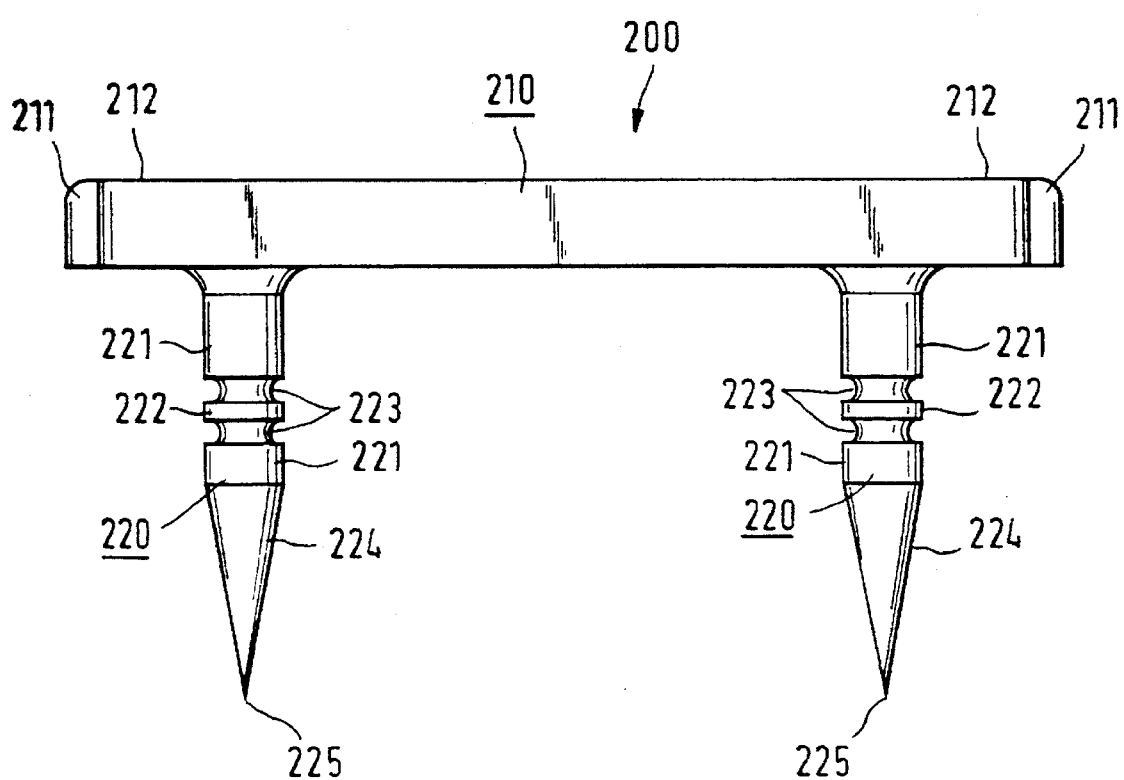
FIG. 4 is an elevational view of another embodiment of the fastener of the present invention.

FIG. 4 illustrates an embodiment of the fastener of the present invention having a single serration. As with the double serrated embodiment 100, single serrated fastener 200 includes backspan 210 and prongs 220 having a shaft portion 221 and circumferential serrations including ridge 222 and recessed notch portions 223. Each prong 220 of fastener 200 also includes a tapered tip portion 224 having a sharp point 225 at its distal end. The backspan 210 can also include overlap portions 212 to increase the surface area of tissue held down and guide members 211 for engagement by a fastener instrument. Fastener 200 differs from fastener 100 in that it includes a single ridge 222 instead of double ridges on each prong. Thus the retention period of fastener 200 will be less than that of fastener 100. As with the previous embodiment, the ridge 222 does not extend radially beyond the circumferential surface of the cylindrical shaft portion. Also, it may be noted that the serrated portion can optionally be located relatively further up the half portion as shown so that there is cylindrical shaft portion 221 below as well as above the serrated portion.

Figure 5:
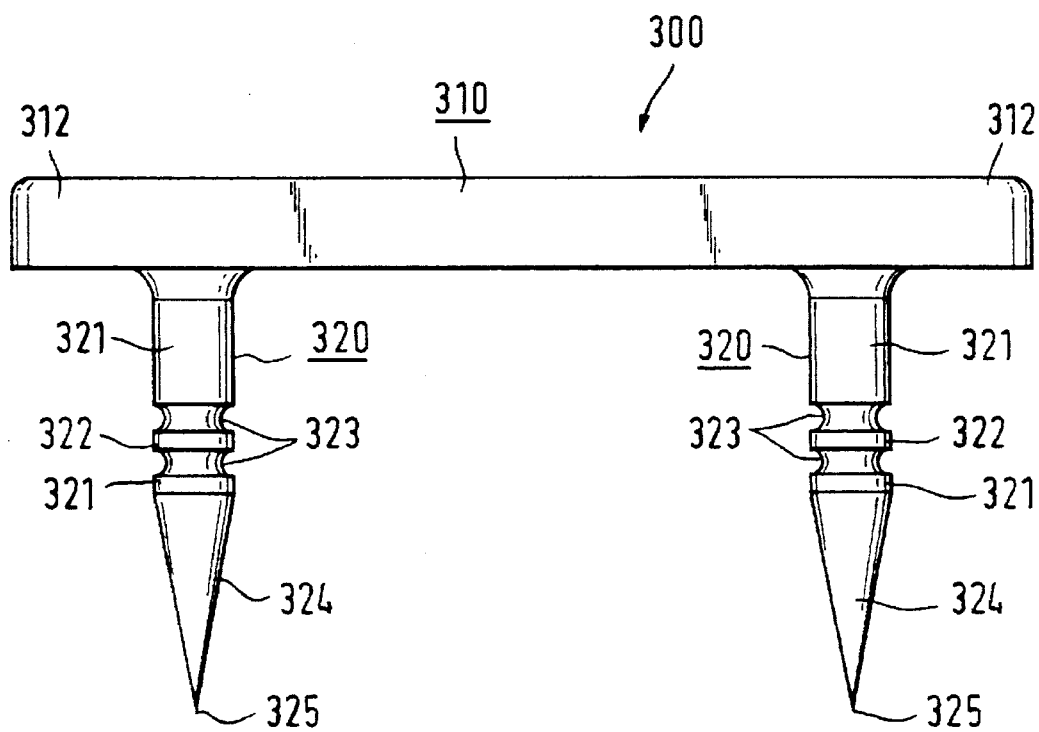
FIG. 5 is an elevational front view of yet another embodiment of a fastener of the present invention.
Figure 6:
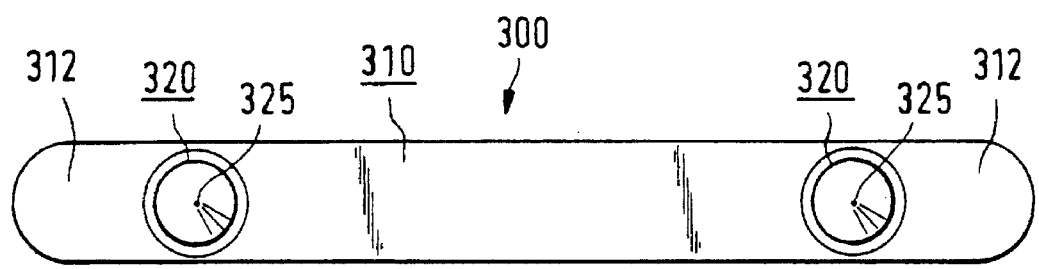
FIG. 6 is a top view of the fastener of FIG. 5.

Fastener 300 of FIGS. 5 and 6 illustrates an embodiment of the present invention which does not have guide members. Parallel prongs 320 illustratively extend perpendicularly from backspan 310. Each prong 320 has a shaft portion 321 preferably circular in cross section. Prongs 320 each have a serrated area with a ridge 322 and notches 323. The prong 320 includes a tip portion 324 terminating in sharp point 325. The backspan 310 includes overlap portion 312. Fastener 300, as shown, does not include a guide member at the ends of the backspan such as in members 111 and 211.

Figure 7:
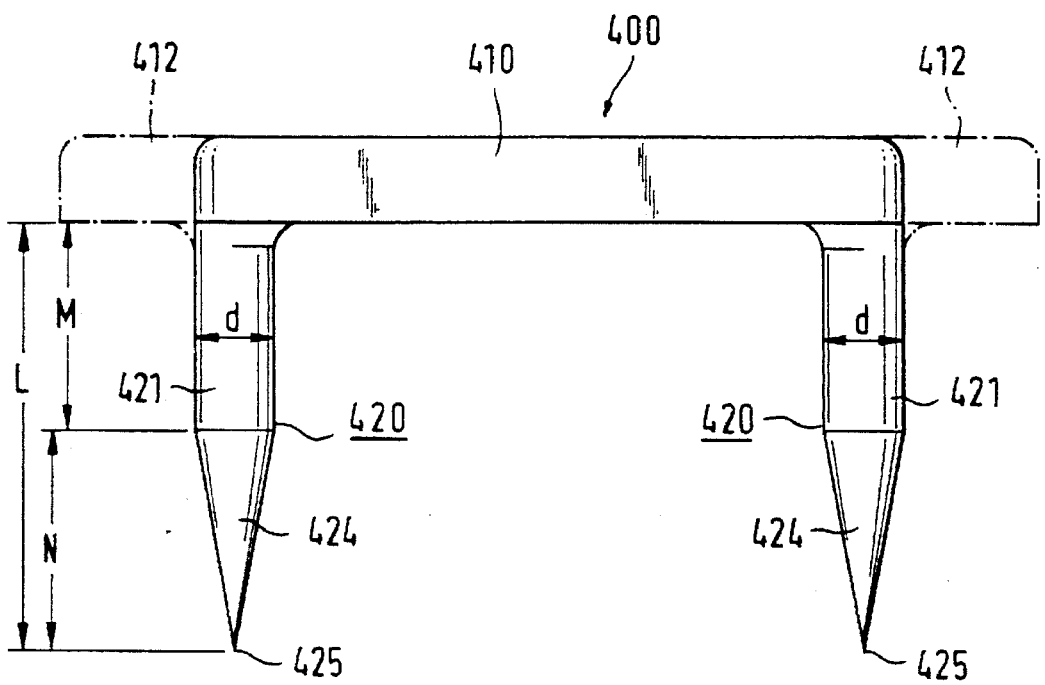
FIG. 7 is an elevational front view of still another embodiment of a fastener of the present invention.
Figure 8:
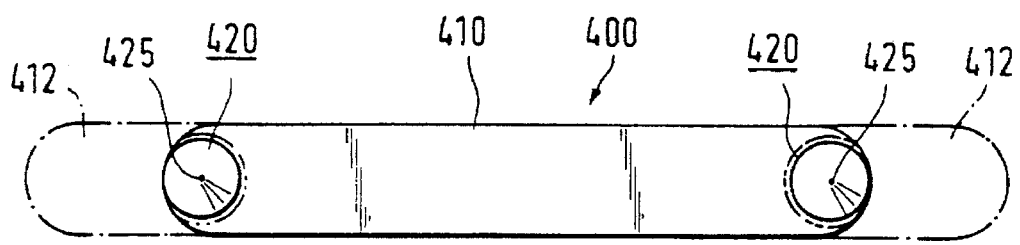
FIG. 8 is a top view of the fastener of FIG. 7.

FIGS. 7 and 8 illustrate another embodiment of the present invention. Fastener 400 includes a backspan 410 and pair of prongs 420 extending from the backspan 410. In this illustrated embodiment, prongs 420 are parallel to one another and extend substantially perpendicular to backspan 410. Each prong has a shaft portion 421 and a tapered tip portion 424 having a sharp distal point 425. Unlike the previous embodiments, fastener 400 does not include serrations so that each shaft portion 421 maintains a substantially smooth continuous surface throughout its length M. Thus, fastener 400 is configured to remain implanted for a shorter period of time than the serrated versions of the fastener shown in FIGS. 1–6. Overlap portion 412 is an optional feature.

Referring to FIG. 7, each prong 420 has an overall length L and the smooth cylindrical shaft portion 421 of each prong 420 has length N and the tapered portion 424 has length M.

Fastener 400 can be fabricated in a variety of sizes. In a longer pronged version, the length M of the shaft portion 421 is about one-half of the overall prong length L, and in a shorter pronged version shaft portion 421 is about one third of the overall prong length L. (Note that fasteners 100, 200 and 300 described above can also be fabricated in a variety of sizes including a long pronged version and a short pronged version.) Clearly, the ratio of the lengths of the shaft portions, tip portion and overall prong can differ from that described above to accommodate various uses of the fasteners.

Figure 9:
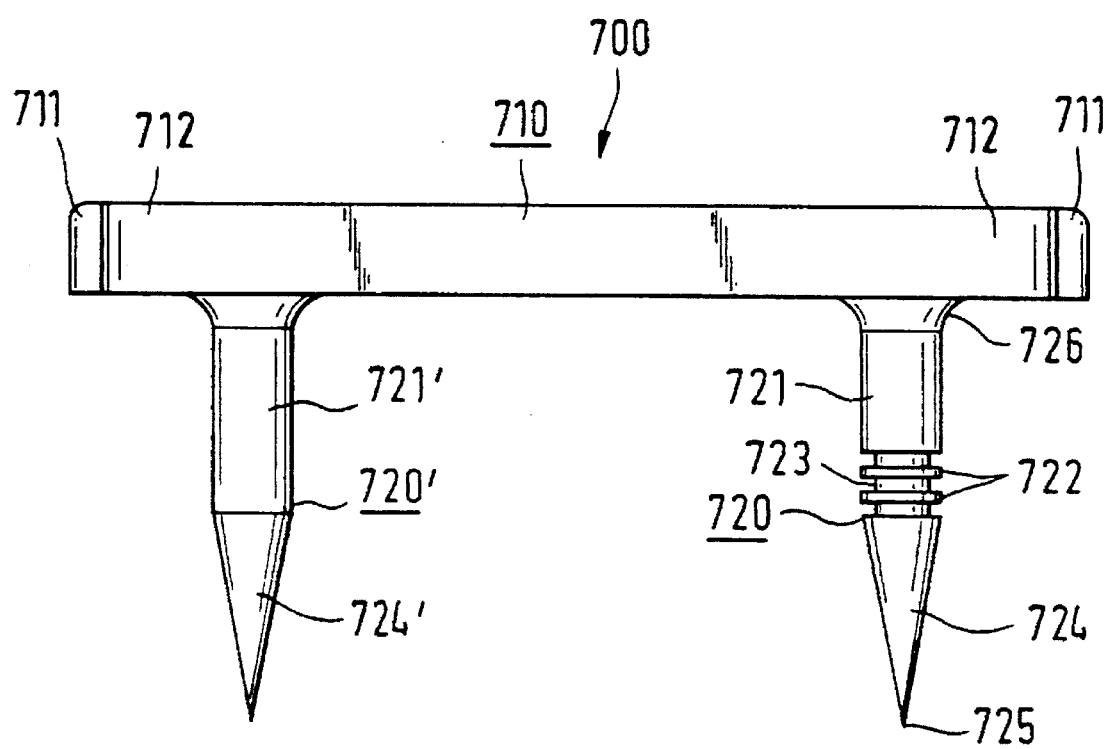
FIG. 9 is an elevational front view of yet another embodiment of a fastener of the present invention.

FIG. 9 illustrates yet another embodiment of the present invention in which fastener 700 has a backspan 710 and a pair of prongs 720, 720'. Backspan 710 is shown with the optional features of the overlap portion 712 and guide members 711. In this embodiment, prong 720' is devoid of serrations and has a continuous smooth surface extending along the length of shaft portion 721' (from backspan 710 to tapered tip portion 724'.) Prong 720 has a double serration formed by ridges 722 and recesses 723 disposed in shaft portion 721. Tapered portion 724 terminates in distal point 725. Due to this configuration, prong 720' has increased frictional characteristics compared to prong 720 and will therefore provide increased holding force of the tissue. This is useful to accommodate differences in tissue type or tissue condition (e.g. health) between adjacent tissue sections to be joined. Thus, the configuration of the prongs of FIG. 9 are suitable when one of the tissue sections requires additional vertical retention force. Clearly, other variations on the number of serrations on each individual prong of the fastener is contemplated by the present invention, and will depend on its use. This advantageously improves the versatility of the fastener by enabling it to accommodate differences in the tissue regions through which it is inserted and adapted to be retained. That is, if additional retention properties are required for only one prong, then additional serrations can be provided on that prong.

Figure 10A:
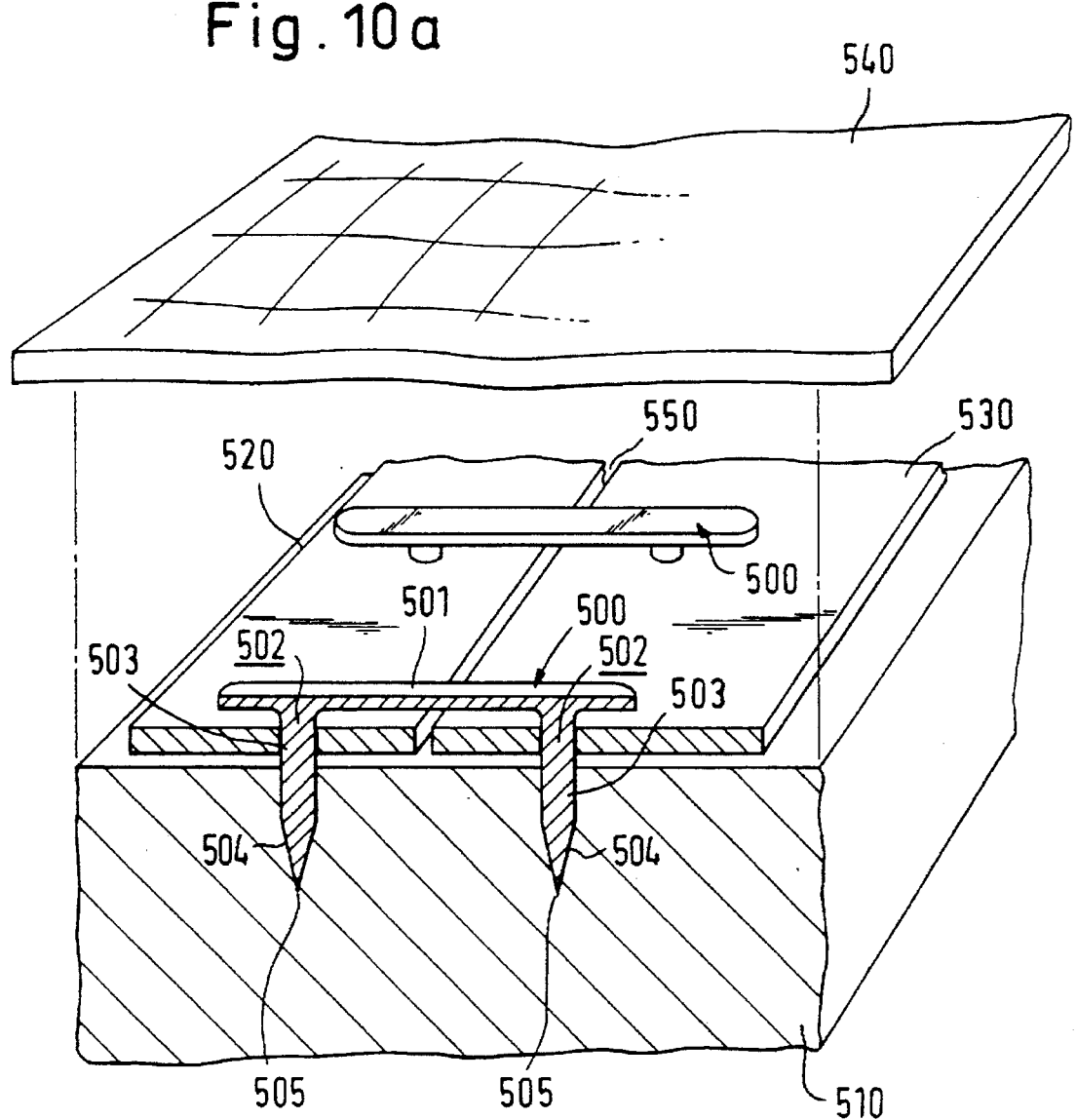
FIGS. 10a and 10b are sectional perspective views illustrating the use of a fastener of the present invention.
Figure 10B:
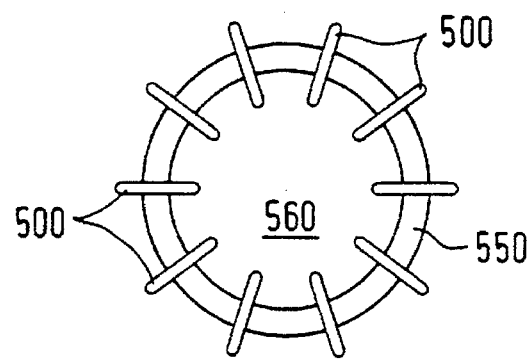
Figure 11:
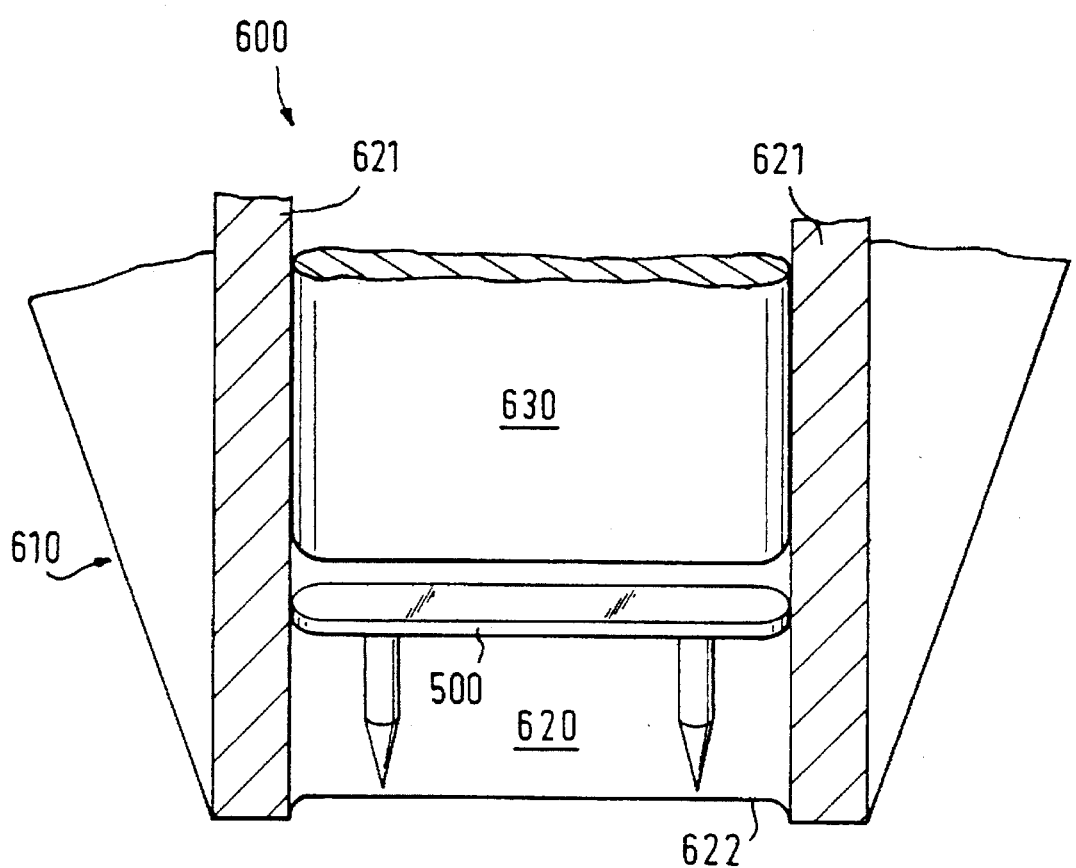
FIG. 11 is a partially cut away elevational view showing an implement for applying a fastener of the present invention.

FIGS. 10a, 10b and 11 illustrate one me of the fastener of the present invention. As shown, the method of skin grafting utilizing the pronged fasteners involves placing a grafted layer of skin 520 adjacent original skin portion 530. Fasteners 500, which can be any of the previously described embodiments, but is shown as a version with no serrations for convenience, are implanted across the interface 550 between a grafted layer of skin 520 and original skin 530. Prongs 502 penetrate the underlying tissue 510 and backspan 501 overlies the upper surface of layers 520 and 530. The fastener 500 thus provides sufficient lateral force across the interface 550. As shown, the prongs of the fastener extend substantially in the same direction. Each tip portion 504 tapers to sharp point 505 to facilitate implementation. In FIG. 10b a grafted layer of skin 550 is placed over an existing wound and skin fasteners 500 are applied circumferentially around the skin layer 550 to fasten it to underlying skin layer 560. Note one of the prongs of the fastener extends into one skin portion and the other prong extends into the other skin portion.

In use, after insertion of the fasteners, gauze dressing 540 is applied over the grafted area and secured by surgical tape, or other suitable means. The gauze dressing provides vertical holding means for the fasteners. Thus, the fasteners principally function to secure the tissue layers 520 and 530 laterally across interface 550. Barbs are not needed to secure grafted layer 520 into base layer 510 since sufficient vertical force is provided by the gauze 540 for the limited time period necessary for healing to commence. That is, the fasteners 500 are only required to in the tissue for a period of time sufficient for healing to begin: typically three to thirteen days and preferably only three days. The smooth surfaced embodiment of the present invention, i.e., the embodiment as illustrated in FIGS. 7 and 8, will typically remain implanted for about 3 to 6 days, although the time periods will differ depending on the configuration of the prong, its material composition and the type and condition of the tissue in which it is embedded as will be described below. The serrated embodiments, on the other hand, will typically remain implanted for a longer period of time and about 5 to 10 days, although the time periods will also differ depending on the aforementioned variables. The fasteners can be ejected by the body or during routine contact such as dressing changes or sponge baths. This advantageously not only saves true which would otherwise be required to remove each fastener but reduces the patient's discomfort and pain caused by such removal. By not having outwardly extending barbs, the fasteners can also be removed more easily and will inflict less pain upon the patient.

An apparatus suitable for applying the skin fasteners of the present invention is disclosed in FIG. 11. The apparatus however, is illustrated for the readers convenience and is not part of the present invention. A fastener applying instrument 600 includes a nose portion 610 having a firing chamber 620 defined by walls 621 and terminating in exit opening 622 at the distal end of the instrument. When used, the distal end of the instrument is positioned adjacent the body tissue to be fastened such that fastener 500 will be implanted into the tissue upon exiting from opening 622. Fastener 500 is slidably positioned in the interior of the firing chamber 620 such that when pusher bar 630 moves distally (i.e. towards exit opening 622), fastener 600 is driven out of the exit opening 622 and into the body tissue. Instruments for holding one or more fasteners and for driving pusher bars are well known to those with skill in the art.

As noted above, one factor affecting the retention period of the fastener is its configuration. The number of serrations formed in the prong will affect the retention time of the fastener; the retention time increasing as the number of serrations increase. The width and length of the prongs will also affect retention time; i.e. the longer fastener taking a longer time to be forced out by the body became of the longer distance it needs to travel through the tissue.

The material utilized for the fastener will also affect the retention period. The desired properties of the material include resiliency, sufficient rigidity to provide lateral force but not too brittle so as to easily break during use. Both bioabsorbable and non-bioabsorbable materials can be urged. Examples of bioabsorbable material include homopolymers or copolymers of lactide, glycolide, polydioxanone, trimethylene carbonate, polyethylene oxide or other bioabsorbable polymer materials or blends of these respective copolymers. One preferred material is made of a copolymer of lactide and glycolide made from approximately 25% m glycolide and 75% m lactide blended with a homopolymer of polyglycolide so the total composition is composed of approximately 42% glycolide. Another bioabsorbable resinous material for constructing the fasteners is disclosed in U.S. Pat. No. 4,523,591 to Kaplan et al, herein incorporated by reference. Clearly, the materials disclosed in the patents and literature listed in the Background section of this application can also be utilized. Non bioabsorbable materials contemplated include any implantable material such as polyester, polypropylene, or polyethylene. Additives can also be mixed with these materials to provide increased stiffening. Materials providing a wetted surface with a low coefficient of friction will facilitate ease of withdrawal from the tissue. Clearly, materials having a higher coefficient of friction will have a relatively longer retention period.

Another factor which can influence the retention period is the interaction between the type of material and the tissue during healing. Increased tissue reactions such as swelling can expedite forcing the fastener towards the surface and out of the tissue. The thickness and type of tissue will also be a factor in retention of the fastener.

The fasteners of the invention can be made of various sizes depending on their use. For example, the length of the backspan and prongs can range from less than one millimeter to over one inch in length, depending on the type of tissue in which they are used. For example, the face and finger regions require a shorter shaft while the abdomen region may require a longer shaft. The length and width of the fastener is a function of the tissue used as well as the material.

Figure 12B:
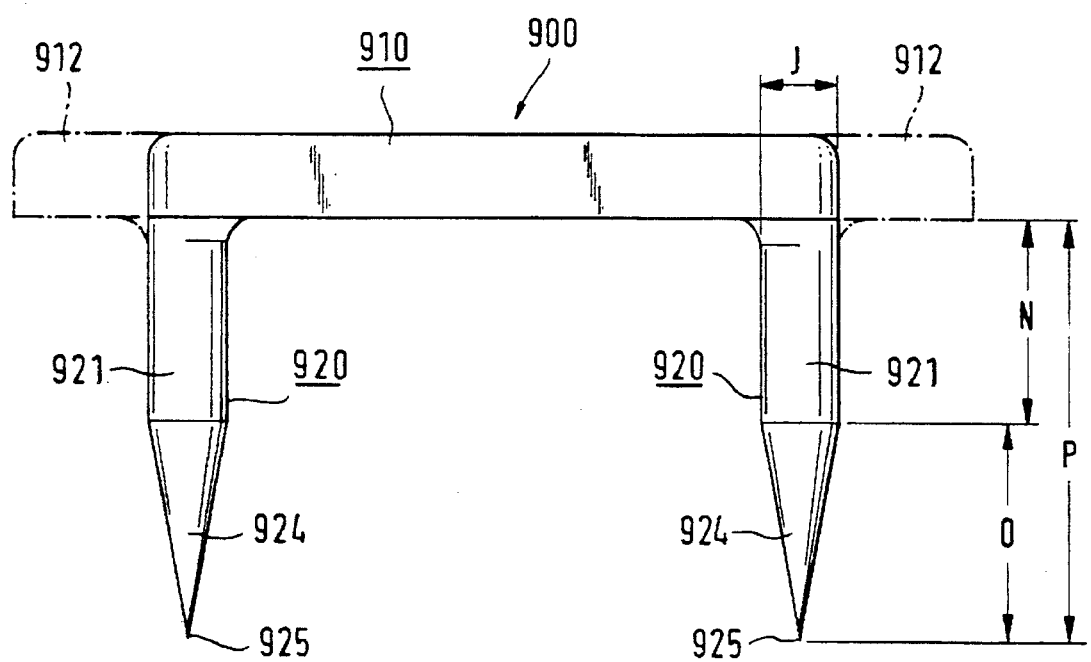
FIGS. 12a and 12b are a top view and an elevational front view, respectively, of an embodiment of a fastener of the present invention labelled to show one example of the dimensions of a non-serrated fastener which can be utilized.
Figure 12A:
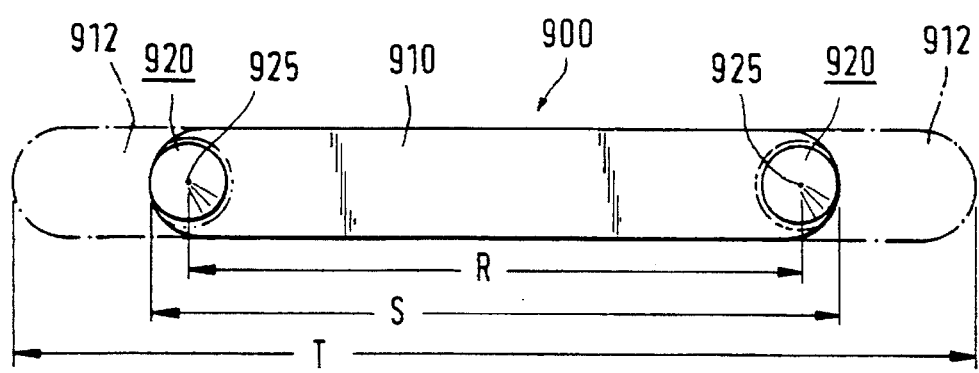
Figure 13:
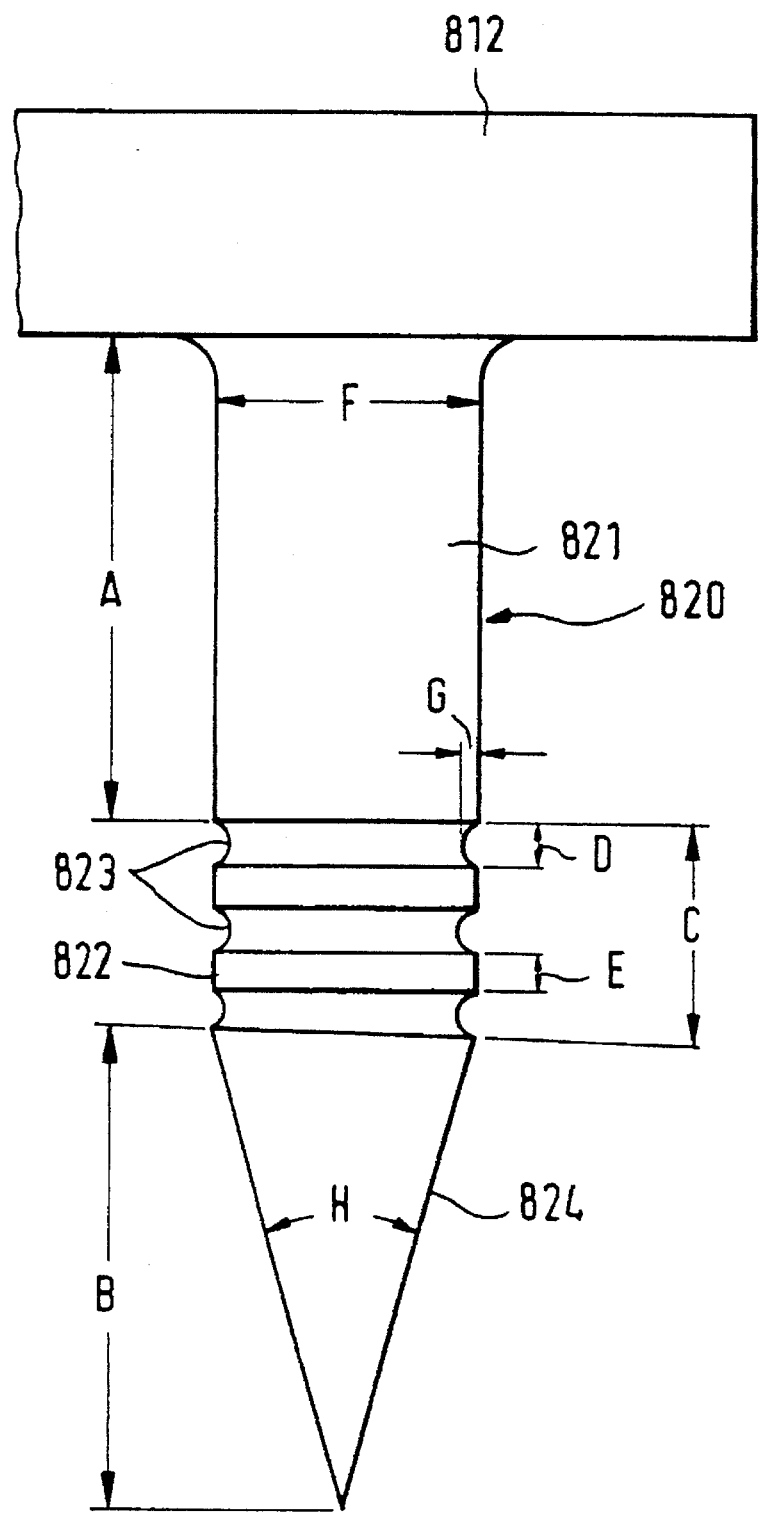
FIG. 13 is an enlarged view of an embodiment of a prong of a fastener of the present invention labelled to show one example of the dimensions of a double serrated fastener which can be utilized.

Set forth below are several examples of dimensions of the fasteners. These dimensions provide only a few examples of the virtually limitless number of sizes in which the fasteners can be formed. Therefore, it should be understood that the following examples of the present invention illustrate only possible dimensions of the fastener, and the fasteners of the present invention are in no way limited to these dimensions. Reference to FIGS. 12a, 12b and 13 will assist in understanding the dimensions set forth below.

In one version the overall length T of backspan 910 of fastener 900 (FIG. 12a), ranges from 0.3985 to 0.3925 inches. Length R ranges from 0.248 to 0.252 inches and length S ranges from 0.2795 to 0.2825 inches. Length J (FIG. 12b) of fastener 900 ranges from 0.030 to 0.032 inches; length N of shaft portion 921 ranges from 0.082 to 0.084 inches; length O of tapered tip portion 925 ranges from 0.082 to 0.084 inches and length P of prong 920 ranges from 0.164 to 0.168 inches.

In a shorter version of fastener 900, length N can range from 0.042 to 0.044, length O from 0.082 to 0.084 and length P from 0.124 to 0.128 inches.

The prong 820 of the fastener of FIG. 13 has a shaft portion 821 of length A and a tapered tip portion 824 of length B, each ranging from 0.082 to 0.084 inches. Diameter F of shaft portion 821 ranges from 0.030 to 0.032 inches. The height D of each notch 823 ranges from 0.008 to 0.011 inches, the depth G of each notch ranges from 0.005 to 0.007 inches, and the height E of each ridge 822 ranges from 0.005 to 0.007 inches. Angle H measures 21° 10'.

It will be understood that the foregoing is only illustrative of the principles of the invention and that various modifications can be made by those skilled in the art without departing from the scope and spirit of the present invention.

What is claimed is:

1. A method of skin grafting utilizing at least one bioabsorbable fastener having a pair of prongs extending from a backspan, each prong having a penetrating tip and a shaft portion; the method comprising the steps of:

a. obtaining a first portion of skin from a portion of the patient's body;

b. placing said first portion of skin adjacent a second portion of skin;

c. providing at least one bioabsorbable fastener having a recessed portion in the shaft portion, wherein said at least one fastener is composed in whole or in part of a homopolymer or copolymer of glycolide, lactide, polydioxanone, trimethylene carbonate, polyethylene oxide or blends thereof;

d. inserting said at least one bioabsorbable fastener having the recessed portion formed in the shaft portion such that said prongs extend through said first portion of skin and a portion of skin extends into the recessed portion, said prongs positioned therein without engaging a retainer; and e. placing a bandage over the backspan of said at least one fastener to apply a force to said fastener.

2. A method as recited in claim 1, wherein said at least one fastener is configured and dimensioned to be ejected from the body after a period of time.

3. A method of skin grafting utilizing at least one bioabsorbable fastener having first and second prongs extending from a backspan, the method comprising the steps of:

a. obtaining a first portion of skin from a portion of the patient's body;

b. placing said first portion of skin adjacent a second portion of skin;

c. inserting said at least one bioabsorbable fastener such that said first prong extends into said first skin portion and said second prong extends into said second skin portion, said at least one fastener positioned therein without engaging a retainer; and d. placing a bandage over the backspan of said at least one fastener to apply a force to said fastener.

4. A method according to claim 3, wherein said at least one fastener is composed in whole or in part of a homopolymer or copolymer of glycolide, lactide, polydioxanone, trimethylene carbonate, polyethylene oxide or blends thereof.

5. A method as recited in claim 3, further comprising the step of leaving said at least one fastener in said skin portion, said at least one fastener being configured and dimensioned to be ejected from the body after a period of time.

6. A method of skin grafting utilizing at least one bioabsorbable fastener having first and second prongs extending from a backspan, the method comprising the steps of:

a. obtaining a first portion of skin from a portion of the patient's body;

b. placing said first portion of skin adjacent a second portion of skin;

c. providing at least one bioabsorbable fastener devoid of barbs; and d. positioning said at least one bioabsorbable fastener such that said first prong extends into said first skin portion in a first direction and said second prong extends into said second skin portion in said first direction, said at least one fastener positioned therein without engaging a retainer; and e. leaving said at least one fastener in said skin portion such that said first and second prongs extend substantially in said first direction and such that said at least one fastener being devoid of barbs can be ejected from the body after a period limited of time.

7. A method according to claim 6 further comprising the step of placing a bandage over the backspan of said at least one fastener to apply a force to said fastener.

8. A method as recited in claim 7 wherein said at least one fastener is configured and dimensioned to be ejected from the body after a period of time.

* * * * *